United States Patent [19]

Ahmed et al.

[11] Patent Number: 5,290,871
[45] Date of Patent: Mar. 1, 1994

[54] GRAFTED COPOLYMERS HIGHLY ABSORBENT TO AQUEOUS ELECTROLYTE SOLUTIONS

[75] Inventors: Iqbal Ahmed, Bartlesville, Okla.; Henry L. Hsieh, Pittboro, N.C.

[73] Assignee: Phillips Petroleum Company, Bartlesville, Okla.

[21] Appl. No.: 65,829

[22] Filed: May 21, 1993

Related U.S. Application Data

[60] Division of Ser. No. 919,075, Jul. 23, 1992, Pat. No. 5,214,117, which is a continuation of Ser. No. 632,226, Dec. 20, 1990, abandoned.

[51] Int. Cl.⁵ .................. C08F 255/00; C08F 265/00; C08F 267/00; C08F 273/00
[52] U.S. Cl. ................................... 525/291; 525/293; 525/319; 525/326.1; 525/331.9; 525/333.3; 525/343
[58] Field of Search ............ 525/291, 293, 319, 326.1, 525/331.9, 333.3, 343

[56] References Cited

U.S. PATENT DOCUMENTS

| | | | |
|---|---|---|---|
| 3,050,390 | 8/1962 | Levinos et al. | 96/35 |
| 3,478,001 | 11/1969 | Szita et al. | 260/79.3 |
| 4,251,651 | 2/1981 | Kawakami et al. | 526/204 |
| 4,403,063 | 9/1983 | Maslanka et al. | 524/531 |
| 4,440,228 | 4/1984 | Swanson | 166/274 |
| 4,460,732 | 7/1984 | Buscall | 524/240 |
| 4,471,097 | 9/1984 | Uhl et al. | 526/240 |
| 4,644,020 | 2/1987 | Stahl | 522/79 |
| 4,666,964 | 5/1987 | Hunter et al. | 524/106 |

OTHER PUBLICATIONS

Salamone et al "Aqueous Salt Absorption by Ampholytic Polysaccharides" Polymer, vol. 26, 1985.
Salamone et al "Polymerization of Ion-Pair Comonomers of Related Structures" J. Macromol. Sci-Chem. A22 (5-7) pp. 653-644 (1985).
Salamone et al "Behavior of Polyampholytes in Aqueous Salt Solution", ACS-Polymeric Materials Science and Engineering, vol. 55, Fall, 1986.
Salamone et al "Synthesis and Solution Properties of Ampholytic Acrylamide Inonomers", J. Macromol. Sci-Chem. A25 (5-7), pp. 811-837 (1988).
Ceresa, ed. Block and Graft Copolymerization, N.Y. John Wiley and Sons (1973) pp. 1-44.
Salamone et al, "Aqueous Solution Properties of a Poly (Vinyl Imidazolium Sulphobetaine)", Polymer, vol. 19, pp. 1057-1078.
Salamone et al "Acrylic Ampholytic Ionomers", Polymers, vol. 23, pp. 843-898 (1982).
Salamone et al "Drag Reduction by Acrylamide Copolymers" Current Topics on Polymer Science, vol. 1, Ed, by Ottenbrite et al, Hanser Publications (1987), pp. 292-301.
Salamone et al. "Synthesis and Aqueous Solution Viscosity Behavior of Polyampholytes from Cationic-Anionic Pairs," Adv. Chem. Sci. 182, pp. 337-346, Chapter 22.

Primary Examiner—Nathan M. Nutter
Attorney, Agent, or Firm—Cynthia L. Stokes

[57] ABSTRACT

The present invention provides graft copolymers that are highly absorbent to aqueous electrolyte solutions. The graft copolymer is formed by the graft polymerizing an effective amount of each of the following components together to provide a highly absorbent copolymer:

(a) graft polymerizing onto a first polymer selected from the group consisting of polysaccharide, polypropylene, polyethylene and other polyolefins, and at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, and any combination of two or more thereof; and (b) graft polymerizing therewith an ampholytic ion pair monomer comprising
  (i) an ammonium cation 2-methacryloyloxyethyldimethylammonium and
  (ii) a sulfonate anion selected from the group consisting of 2-acrylamido-2-methylpropane sulfonate, 2-methacryloyloxyethane sulfonate, vinyl sulfonate, styrene sulfonate and any combination of thereof.

22 Claims, No Drawings

GRAFTED COPOLYMERS HIGHLY ABSORBENT TO AQUEOUS ELECTROLYTE SOLUTIONS

This application is a Divisional Application of prior application Ser. No. 07/919,075, filed Jul. 23, 1992, now U.S. Pat. No. 5,214,117 which is a continuation under 37 C.F.R. 1.62, of application Ser. No. 07/632,226, filed Dec. 20, 1990, now abandoned.

BACKGROUND OF THE INVENTION

1. Field of the Invention

This invention pertains to graft copolymers made with 2-methacryloyloxyethyldimethylammonium (MEDMA)/sulfonate ion pairs which are useful for absorbing aqueous electrolyte solutions. A further aspect of the invention relates to a method of using graft copolymers made with 2-methacryloyloxyethyldimethylammonium/sulfonate ion pairs for absorbing aqueous electrolyte solutions.

2. Description of the Prior Art

Polymers for absorbing aqueous electrolyte solutions are used in numerous commercial and industrial applications. For example, polymers are used to improve the water absorbency of paper towels and disposable diapers.

Though known water absorbing polymers are highly absorbent to deionized water, they are dramatically less absorbent to aqueous electrolyte solutions such as salt water, brine, and urine. For example, hydrolyzed cross-linked polyacrylamide absorbs 1,024 grams of deionized water per gram of polymer, but only 25 grams of synthetic urine per gram of polymer. Cross-linked polyacrylate absorbs 423 grams of deionized water per gram of polymer, but only 10 grams of synthetic urine per gram of polymer. Hydrolyzed cross-linked polyacrylonitrile absorbs 352 grams of deionized water per gram of polymer, but only 25 grams of synthetic urine per gram of polymer. Analogous starch grafted copolymers generally have very poor absorbency to synthetic urine.

It would be a valuable contribution to the art to develop graft copolymers with high absorbency to aqueous electrolyte solutions. It also would be a valuable contribution to the art to develop inexpensive graft copolymers with high absorbency to aqueous electrolyte solutions. Furthermore, it would be a valuable contribution to the art to develop biodegradeable graft copolymers which were high absorbency to aqueous electrolyte solutions. The market for these types of copolymers is large and the uses are numerous. Therefore, seemingly small improvements in the absorbency translate into large savings in the quantity of copolymer required to absorb these liquids and large savings to the consumer.

Thus, it is a object of the present invention to provide graft MEDMA/sulfonate copolymers which are highly absorbent to aqueous electrolyte solutions.

Another object of the present invention is to provide highly biodegradeable graft copolymers which are highly absorbent to aqueous electrolyte solutions.

A further object of the present invention is to provide a method of using the graft copolymers of the present invention for absorbing an aqueous electrolyte solution comprising the step of contacting the graft copolymers of the present invention with the aqueous electrolyte solution.

Further objects, features, and advantages of the present invention will be readily apparent to those skilled in the art upon reading the description of the invention which follows.

SUMMARY OF THE INVENTION

The graft copolymers of the present invention are graft copolymers formed by:

(A) graft copolymerizing onto a first polymer selected from the group consisting of polysaccharide, polypropylene, polyethylene and other polyolefins, and at least one comonomer, selected from the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and any combination of two or more thereof; and (B) graft copolymerizing therewith an ampholytic ion pair monomer having an ammonium cation and a sulfonate anion wherein
  (i) the ammonium cation is 2-methacryloyloxyethyldimethylammonium and
  (ii) the sulfonate anion is selected from the group consisting of 2-acrylamido-2-methylpropane sulfonate, 2-methacryloyloxyethane sulfonate, vinyl sulfonate, styrene sulfonate, and any combination of two or more thereof; wherein the first polymer, comonomers and ion pair monomers are provided in amounts which are effective to produce a highly absorbent graft copolymer.

A further aspect of the invention relates to a method of absorbing an aqueous electrolyte solution comprising (A) contacting a graft copolymers formed by
  (i) graft copolymerizing onto a first polymer selected from the group consisting of polysaccharide, polypropylene, polyethylene and other polyolefins, and at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and any combination of two or more thereof; and
  (ii) graft copolymerizing therewith an ampholytic ion pair monomer having a ammonium cation and a sulfonate anion wherein
    (a) the ammonium cation is 2-methacryloyloxyethyldimethylammonium; and
    (b) the sulfonate anion is selected from the group consisting of 2-acrylamido-2-methylpropane sulfonate, 2-methacryloyloxyethane sulfonate, vinyl sulfonate, styrene sulfonate and any combination of two or more thereof; wherein the first polymer, comonomers and ion pair monomers are provided in amounts which are effective to produce a highly absorbent graft copolymer; with an aqueous electrolyte solution.

DESCRIPTION OF THE INVENTION

The present invention provides graft copolymers that are highly absorbent to aqueous electrolyte solutions. The graft copolymers of the present invention utilize an ampholytic ion pair composed of a 2-methacryloyloxyethyldimethylammonium cation and a sulfonate anion.

Graft copolymers as used herein are polymers of one or more species of monomers connected to a main chain as a side chain, exclusive of branch point on the main chain. Side chains of a graft copolymer are distinguished from the main polymer chain by the monomer constitution of the side chain i.e., the side chains comprise units derived from at least one species of monomer different from those that supply the units of the main polymer chain. The main polymer chain as utilized in the present invention are homopolymeric and copolymeric polymer such as polysaccharide, polypropylene, polyethylene and other polyolefins. The side chains are formed of olefinic comonomers and ampholytic ion pairs.

The term "graft copolymerization" is used herein, unless otherwise indicated, to mean a copolymer which results from the formation of an active site or sites at one or more points on the main chain of a polymer molecule other than its end and exposure to at least one other monomer. The graft copolymers of the present invention comprise graft copolymers formed by graft copolymerization of an effective amount of each of the following components onto a first polymer (main polymer chain) to produce a highly absorbent copolymer:

(A) at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and combination of two or more thereof; to form a first graft copolymer and (B) an ampholytic ion pair monomer comprising
  (i) the ammonium cation 2-methacryloyloxyethyldimethylammonium (also referred to as MEDMA) and
  (ii) a sulfonate anion selected from the group consisting of 2-acrylamido-2-methylpropane sulfonate (also referred to as AMPS ® a trademark of Lubrizol for 2-acrylamido-2-methylpropane sulfonic acid), 2-methacryloyloxyethane sulfonate (also referred to as MES), vinyl sulfonate and styrene sulfonate and any combination thereof.

Polymer or copolymer which may be used as main chains in the practice of the present invention include polysaccharides, polypropylene, polyethylene and other polyolefins. Polysaccharides suitable for the practice of the present invention include starches, celluloses and glycogens. Common sources of cellulose include but are not limited to cotton, linen, rayon, wood pulp and cellulose xanthine. Currently, cotton gauze is preferred. Suitable starches included swollen amylose and amylopectin starches. For the practice of the present invention, these starches should be swollen by heating the starch in water to substantially dissolve the starch granules. Preferably starches used in the present invention will have less than 30 weight percent amylose based on the weight of the dry starch before graft copolymerization. The preferred starch for use in grafting is soluble starch flour with in the range of from about 0 to about 20 weight percent amylose content. Polypropylene polymer suitable for use as main polymer chain include polypropylene homopolymers, polypropylene copolymers and polypropylene block-copolymers. Polyethylene polymers suitable for use as a main polymer chain include polyethylene homopolymer, polyethylene copolymers and polyethylene block-copolymers. Preferably the synthetic polymers listed above will be utilized in the form of filaments or thin sheets so that a high surface area to mass will be provided for grafting the comonomers and ampholytic ion pair onto. Filaments utilized for grafting will preferably have a denier ranging from about 1 to about 20 denier and most preferably from in the range of about 1 to 8 denier.

The term "monomer" is used generically, unless otherwise indicated, to mean monomers, comonomers, termonomers, tetramonomers, etc. The term "comonomer" is used generically, unless otherwise indicated, to mean monomers, comonomers, termonomers, tetramonomers, etc. for polymers wherein there are at least two different monomers.

The term "polymer" is used unless otherwise indicated, to mean homopolymers, copolymers, terpolymers, tetrapolymers, etc., and grafted copolymers thereof. The term "copolymer" is used generically, unless otherwise indicated, to mean copolymers, terpolymers, tetrapolymers, etc., thus includes polymer prepared using two or more different monomers.

The olefinic comonomers can include but are not limited to the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid and N-vinyl-2-pyrrolidone.

As used in this application, the term "alkali salts" is used generically, unless otherwise indicated to mean alkali salts including but not limited to lithium, sodium, potassium, and ammonium cations.

The ampholytic ion pair monomer used in the present invention may be prepared by titrating an aqueous solution of a sulfonic acid monomer to pH 7 with 2-methacryloyloxyethyldimethylamine at a temperature of about 0°–15° C. The resulting aqueous solution containing the ampholytic ion pair may be purified by contacting the aqueous solution one or more times with small quantities of activated charcoal. The concentration of the ampholytic ion pair in the aqueous solution may be determined by evaporatively drying a known amount of the aqueous solution and weighting the residue.

Alternatively, the ampholytic ion pair monomer for use in the practice of the present invention may be prepared by methods which are well known to those skilled in the art. For example, one of the ampholytic ion pair monomers can be prepared by reacting 2-methacryloyloxyethyldimethylamine with commercially available 2-acrylamido-2-methylpropane sulfonic acid or 2-methacryloyloxyethane sulfonic acid in anhydrous tetrahydrofuran. See J. C. Salamone, C. C. Tsai, A. P. Olson, and A. C. Watterson, *Adv. Chemical Series*, Volume 187, pages 337–346.

The polymers of the present invention were generally prepared in a two step process, though a single graft copolymerizing step or more than two grafting and polymerizing steps may be advantageously employed. The purpose of the two step process is to provide a first grafted polymer wherein the grafted comonomer side chains are more reactive to the polymerization of the ampholytic ion pair monomer. Some systems may be reactive enough so that a two step process is not necessary to provide grafted copolymers which are highly absorbent to aqueous electrolyte solutions. Alternatively, the multiple step process may be advantageously employed to control the proportions of monomers and relative lengths of the block copolymer chains by graft copolymerizing the various monomers in the desired stoichiometric ratios at the appropriate step of the process.

In the preparation of polysaccharide graft MED-MA/sulfonate copolymers it is preferred that as a first step, at least one of the comonomers is graft copolymerized onto a polysaccharide, to produce a first polysaccharide graft copolymer. Then in a second step, the ampholytic ion pair is graft copolymerized onto the polysaccharide or the ampholytic ion pair is polymerized onto the grafted comonomer side chains. At the second or any subsequent graft copolymerizing step, the ampholytic ion pair monomer may be copolymerized with at least one other comonomer. At the second step or any subsequent graft copolymerizing step, the ampholytic ion pair monomer may be copolymerized with at least one comonomer which has a polymerizable olefinic functionality selected from the group consisting of acrylamide (also referred to as AM), methacrylamide, acrylonitrile (also referred to as AN), acrylic acid (also referred to as AA), methacrylic acid, alkali salts of acrylic acid (also referred to as X–AA), alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and any combination of two or more thereof.

The polymerization of the ampolytic ion pair may require a higher temperature than the polymerization of some of the other comonomers. Therefore, for the polymerization of the ampolytic ion pair it is desirable to perform the polymerization at temperatures in the range of from about 0° C. to about 90° C. and preferably in the range of from about 40° C. to about 70° C. Those skilled in the art will recognize that the temperatures at which the polymerization is carried out should be varied to allow the various monomers and comonomer to react completely within a reasonable period of time for the method of polymerization utilized.

Most graft copolymerization methods for olefinic monomers involve the creation of reactive sites (for example free-radicals) on the main polymer chain. These reactive sites then serve to initiate the copolymerization of the other monomers onto the main copolymer chain. Free-radicals reactive sites on the main chain generally are produced by high energy radiation or chemical initiation. A common chemical means for creating these free-radicals within polysaccharide polymers and polypropylene polymers is with a chemical oxidation-reduction system. Examples of such oxidation-reduction systems include but are not limited to oxidation-reduction systems selected from the group consisting of ceric ammonium nitrate/nitric acid, ceric ammonium sulfate/sulfuric acid, potassium permanganate/oxalic acid, hydrogen peroxide/ferrous alkali salts, hydrogen peroxide/ascorbic acid and amine/persulfate. Common irradiation means for producing free radicals on the main polymer chain is by utilizing a gamma radiation source (i.e. cobalt 60) or an electron beam.

The copolymerization of the ampholytic ion pair monomer with the olefinic comonomer onto the grafted comonomer side chains can be achieved by any of the well known free-radical polymerization techniques in solution, suspension, or emulsion environment. Well known azo compounds commonly employed to initiate free radical polymerization reactions include 2,2'-azobis(N,N'-dimethylisobutyramidine) dihydrochloride, azobisisobutyronitrile, 4,4'-azobis(4-cyanovaleric acid), 2,2'-azobis(2,4-dimethyl(4-methyoxyvaleronitrile), 2,2'-azobis(2,4-dimethylvaleronitrile), 2,2'-azobis(2-amidinopropane)dihydrochloride, 2-t-butylazo-2-cyano-4-methoxy-4-methylpentane, 2-t-butylazo-2-cyano-4-methylpentane, and 4-t-butylazo-4-cyanovaleric acid. Well known inorganic peroxide compounds commonly employed to initiate free radical polymerization reactions include hydrogen peroxide, alkali metal persulfates, alkali metal perborates, alkali metal perphosphates, and alkali metal percarbonates. Well known organic peroxide compounds commonly employed to initiate free radical polymerization reactions include lauryl peroxide, 2,5-dimethyl-2,5-bis(2-ethylhexanylperoxy)hexane, t-butylperoxypivilate, t-butylperoctoate, p-menthane hydroperoxide, and benzoylperoxide. The compound t-butylhyponitrite is a well known alkyl hyponitrite commonly employed to initiate free radical polymerization reactions. Furthermore, ultraviolet light is commonly employed to initiate free radical polymerization reactions with olefinic monomers. In addition, such other methods of copolymerization as would have occurred to one skilled in the art may be employed, and the present invention is not limited to the particular method of preparing the polymer set out herein. The appropriate conditions under which polymerization reaction described above are well known in the art.

Optionally the inventive graft copolymers of the present invention can be crosslinked with a suitable crosslinking agent including but not limited to the group consisting of N,N-diallylmethacrylamide, diallylamine, N,N-bisacrylamidoacetic acid, N,N'-bisacrylamidoacetic acid methylester, N,N'-methylenebisacrylamide (methylene-bis-acrylamide), N,N-benzylidenebisacrylamide, allylacrylate, diisopropenylbenzene, diallylsuccinate, ethyleneglycol diacrylate, diallylacrylamide, divinylbenzene, and combinations of two or more thereof. The crosslinking agent should be admixed with the monomer or comonomers when the side chain are being formed from the main polymer chain. The amount of crosslinking agent admixed with the monomers or comonomers will be in the range of from about 0.01 to about 0.2 weight percent of total weight of monomers and comonomers in the graft copolymerization reaction.

The graft copolymers containing an olefinic comonomer with amide, nitrile, carboxylic acid, or sulfonic acid functionalities can optionally be at least partially hydrolyzed and/or neutralized by heating with aqueous base such as aqueous sodium hydroxide or aqueous potassium hydroxide. As used in this herein, the term "hydrolysis" is used generically, unless otherwise indicated, to include hydrolysis of nitrile functionalities and hydrolysis of amide functionalities. These hydrolysis reactions are loosely referred to in the art as "saponification." Hydrolysis of these functionalities may occur under acidic or basic conditions. Under basic hydrolysis conditions, the term also includes, unless otherwise indicated, neutralization of carboxylic acid and sulfonic acid functionalities. The degree of hydrolysis and/or neutralization can be controlled by stoichiometrically limiting the amount of base relative to the amount of amide, nitrile, carboxylic acid, and sulfonic acid functionalities.

The relative amount of the main polymer chain to the total weight of the comonomer and ampholytic ion pair can be chosen to provide a graft copolymer of variable absorbency. However, it is preferred that the main polymer chain constitutes in the range of from about 1 to about 50 weight percent of the total weight of comonomers, ampholytic ion pair and main polymer chain present and most preferably it is preferred that the amount of main polymer chain be in the range from about 5 to about 30 weight percent. The mole percent of comonomer and ampholytic ion pair which may be graft copolymerized onto the main polymer chain is given in Tables I and II (these mole percents are based on the total moles of the comonomers and ampholytic ion pair totaling a 100 percent).

TABLE I

Broad Comonomer Compositions for the Graft Copolymers

| | MOLE PERCENT | | | |
|---|---|---|---|---|
| | MEDMA/sulfonate | AM | AN | X-AA |
| broad | 2-25 | — | 98-75 | — |
| broad | 2-20 | 98-80 | — | — |
| broad | 2-20 | — | — | 98-80 |

MEDMA/sulfonate = 2-methacryloyloxyethyldimethylammonium cation/a sulfonate anion selected from the group consisting of 2-acrylamido-2-methylpropane sulfonate, 2-methacryloyloxyethane sulfonate and any combination thereof
AM = Acrylamide
AN = Acrylonitrile
X-AA = Alkali Salt of Acrylic Acid

TABLE II

Preferred Comonomer Compositions for the Graft Copolymers

| | MOLE PERCENT | | | | |
|---|---|---|---|---|---|
| | MEDMA/ AMPS ® | MEDMA/MES | AM | AN | X-AA |
| preferred | 7-20 | — | — | 93-80 | — |
| preferred | — | 10-25 | — | 75-90 | — |
| preferred | 5-15 | — | 95-85 | — | — |
| preferred | — | 10-15 | 90-85 | — | — |
| preferred | 3-15 | — | — | — | 97-85 |
| preferred | — | 3-10 | — | — | 97-90 |

MEDMA/MES = 2-methacryloyloxyethyldimethylammonium cation/2-methacryloyloxyethane sulfonate
MEDMA/AMPS ® = 2-methacryloyloxyethylitrimethylammonium cation/2-acrylamido-2-methylpropane sulfonate
AM = Acrylamide
AN = Acrylonitrile
X-AA = Alkali Salt of Acrylic Acid (Acrylate)

The polysaccharide grafted polymers of the present invention should be highly biodegradable because the main chain of the graft copolymer is highly biodegradable.

A further aspect of the invention relates to a method of absorbing aqueous electrolyte solutions comprising the step of contacting the polymers of the present invention with the aqueous solution. Typical aqueous electrolyte solutions include but are not limited to electrolyte solutions selected from the group consisting of tap water, salt water, brine, and urine. For the purpose of this invention, tap water is defined to have an electrolyte concentration of less than 500 ppm of dissolved electrolytes, urine is defined to have an electrolyte concentration of from greater than 500 ppm to at most 10,000 ppm of dissolved electrolytes, salt water is defined to have an electrolyte concentration from greater than 10,000 ppm to at most 34,000 ppm and brine is defined to have an electrolyte concentration of from greater than 34,000 ppm to the saturation point of the solution.

The following examples are intended to illustrate the advantages of this invention but are not intended to unduly limit this invention.

EXAMPLE I

The control data in Table III demonstrates that although known crosslinked polymers are highly absorbent to deionized water, they are dramatically less absorbent to aqueous electrolyte solutions such as salt water and urine. Polysaccharide grafted polymers, however, according to their inherent nature, are normally much less absorbent to aqueous liquids. The polysaccharide substrate, which comprises a large portion of the material, is very poorly absorbent to aqueous liquids of all kinds. This control data can be used to show that the polysaccharide grafted MEDMA/sulfonate copolymers of the present invention can effectively compete with these known crosslinked polymers and exceed the absorbency of these known crosslinked polymers. Furthermore, these known cross-linked polymers have questionable biodegradeability.

Known polymer compositions include crosslinked polyacrylamide, partially saponified crosslinked polyacrylamide, crosslinked polyacrylonitrile, partially saponified cross-linked acrylonitrile, cross-linked polyacrylic acid, neutralized crosslinked polyacrylic acid, cross-linked polyacrylate, and polymers thereof with sodium 2-acrylamido-2-methylpropane sulfonate. The best of these known polymers absorbs up to about 60 grams of urine per gram of polymer, and most of the known polymers absorb much less than 50 grams of urine per gram of polymer.

The crosslinked polymers of the control data were prepared by mixing the monomers in the proportions given in Table III in an aqueous solution of deionized water. The monomers were present in about 30–40 weight percent relative to the amount of deionized water. The free radical polymerization was initiated with commercially available 2,2'-azobis(N,N'-dimethylisobutyramidine) dihydrochloride. The reaction mixture was then degassed by bubbling nitrogen gas through the mixture for 15 minutes. About 0.1 mole percent based on the total moles of the monomers of the azo free-radical initiator was employed. The reaction temperature was maintained between 20°–35° C. for 24 hours. The reactions produced transparent or cloudy hard gels of the crosslinked polymers. A large volume of deionized water was added to the polymer product and the polymers were allowed to swell for about 24 hours. The swelled polymers were dried in a forced convection oven at 74° F. The dried polymers were then mechanically blended into a powder.

Some of the crosslinked polymers were hydrolyzed or neutralized with a strong base such as aqueous sodium hydroxide or aqueous potassium hydroxide. The degree of hydrolysis or neutralization could be controlled by stoichiometrically limiting the amount of base relative to the amount of amide, nitrile, or carboxylic acid functionalities. For these examples, a stoichiometric excess of the amount of base was used. A suspension of 1 gram of the polymer in about 20 milliliters of 0.5 molar aqueous sodium hydroxide was heated to 95° C. until a light golden-yellow color was obtained. The mixture was then transferred to a dialysis bag with a molecular weight cut-off of 12,000-14,000 and dialyzed exhaustively against distilled water until the viscous polymer gel had reached pH 7. This viscous polymer gel was then poured into a plastic dish and dried in a forced convection oven at 74° C. The dried polymers were then mechanically blended to a powder.

The crosslinked polymers were then tested for deionized water absorption and synthetic urine absorption. About 1 liter of deionized water or synthetic urine was added to 0.1 to 0.5 gram of the dried polymer and allowed to stand for 24 hours. The polymer was then separated from the excess unabsorbed liquid by screening through a 100 mesh per inch stainless steel sieve. The absorbency was determined by weighing the isolated polymer containing the absorbed liquid and subtracting the weight of the dry polymer. The absorbency was measured in units of grams of liquid per grams of polymer. The synthetic urine was prepared by dissolving 0.64 gram $CaCl_2$, 1.14 gram $MgSO_4.7H_2O$, 8.20 gram NaCl, and 20.0 gram urea into 1000 gram deionized water. Several of the polymers were tested two or three times, and the experimental error was within plus or minus 2-5 percent. This small experimental error was largely caused by gel blocking and minor diffusion problems that prevented the aqueous liquid from contacting with all the polymer.

cally less absorbent to aqueous electrolyte solutions such as salt water and urine. The commercially available water absorbing materials tested include poly(co-acrylamide-co-acrylic acid) grafted onto starch, a commercial acrylamide polymer sold under the trademark "Water Grabber" ® ("Water Grabber" is a trademark of F. P. Products, Inc.), "LUVS" ® diaper absorbent ("LUVS" is a trademark of Procter & Gamble Co.), "Pampers" ® diaper absorbent ("Pampers" is a trademark of Procter & Gamble Co.), and "Favor 960" ® (Stockhausen, Inc.). The best of these known materials absorb up to about 56 grams of urine per gram of absorbing material, and most of the known polymers absorb much less than 40 grams of urine per gram of absorbing material.

The commercially available materials were tested for absorbency to aqueous liquids according to the method employed in Example I.

TABLE IV

Control Data For Commercial Materials

| EXP# | Commercial Material | g/g D/W | g/g SU |
|---|---|---|---|
| 1 | COMMERCIAL STARCH-g-POLY(AM-AA) | 345 | 37 |
| 2 | WATER GRABBER ® (AM COPOLYMER) | 440 | 34 |
| 3 | LUVS ® DIAPER ABSORBENT | 191 | 16 |
| 4 | PAMPERS ® DIAPER ABSORBENT | 171 | 12 |
| 5 | FAVOR 960 ® | 369 | 56 | g = graft
AM = Acrylamide

TABLE III

Control Data For Known Cross-Linked Polymers

| EXP# | AMPS ® | AM | AN | AA | X-AA | mole ratio* LINK | XOH | g/g** DIW | g/g** SU |
|---|---|---|---|---|---|---|---|---|---|
| 126A | — | 100 | — | — | — | 0.05 | NO | 17 | 15 |
| 126 | — | 100 | — | — | — | 0.05 | YES | 1024 | 25 |
| 406R | — | 100 | — | — | — | 0.05 | YES | 364 | 40 |
| 125A | — | 100 | — | — | — | 0.20 | NO | 13 | 12.5 |
| 125 | — | 100 | — | — | — | 0.20 | YES | 295 | 16 |
| 26 | — | — | 100 | — | — | 0.05 | YES | 608 | 46 |
| 405 | — | — | 100 | — | — | 0.10 | NO | 0 | 0 |
| 405 | — | — | 100 | — | — | 0.10 | YES | 414 | 42 |
| 129 | — | — | 100 | — | — | 0.20 | YES | 352 | 25 |
| 127A | — | — | — | 100 | — | 0.20 | NO | 21 | 11 |
| 127 | — | — | — | 100 | — | 0.20 | Neutr. | 423 | 10 |
| 194 | — | — | — | — | 100(K) | 0.05 | NO | 669 | 57 |
| 204 | — | — | — | — | 100(Na) | 0.05 | NO | 505 | 41 |
| 211 | — | 13 | — | — | 87 | 0.05 | NO | — | 65 |
| 267 | 3 | 13 | — | — | 84 | 0.05 | NO | 350 | 38 |
| 372 | 3 | 20 | — | — | 77 | 0.05 | NO | 417 | 47 |
| 20 | 6 | 13 | — | — | 81 | 0.05 | NO | 738 | 56 |
| 21 | 6 | 26 | — | — | 68 | 0.05 | NO | 533 | 47 |
| 22 | 6 | — | — | — | 94 | 0.05 | NO | 488 | 55 |
| 23 | 10 | 13 | — | — | 77 | 0.05 | NO | 570 | 59 |
| 25 | 20 | 13 | — | — | 67 | 0.05 | NO | 624 | 62 |
| 19 | 100 | — | — | — | — | 0.05 | NO | Soluble | |

AMPS ® = 2-acrylamido-2-methylpropane sulfonate (Note: AMPS ® is a trademark of Lubrizol for 2-acrylamido-2-methylpropane sulfonic acid.)
AM = Acrylamide
AN = Acrylonitrile
AA = Acrylic Acid
X-AA = Sodium Acrylate of Potassium Acrylate
LINK = Methylene-bis-acrylamide CrossLinking Agent
XOH = Basic Hydrolysis and/or Neutraliztion with aquous NaOH or KOH
DIW = Deionized Water
SU = Synthetic Urine
*mole ratio = mole of the crosslinking agent per 100 mole of the ampholytic ion pair monomer and the comonomer
**g/g = absorbency units of gram aqueous liquiid per gram dried polymer

EXAMPLE II

The control data in Table IV demonstrates that although commercially available water absorbing materials are highly absorbent to water, they are also dramati- AA = Acrylic Acid
DIW = Deionized Water
SU = Synthetic Urine
*g/g = absorbency units of gram aqueous liquid per gram dried polymer

EXAMPLE III

The homopolymers of the ampholytic ion pair monomers comprising 2-methacryloyloxyethyldimethylammonium 2-acrylamido-2-methylpropane sulfonate (MEDMA/AMPS) (AMPS ® is a trademark of Lubrizol Corporation for 2-acrylamido-2-methylpropane sulfonic acid) or 2-methacryloyloxyethyldimethylammonium 2-methacryloyloxyethane sulfonate (MEDMA/MES) with 0.05 weight percent methylene-bis-acrylamide crosslinking agent was tested for their absorbency to deionized water and synthetic urine according to the method employed in Example I. The absorbency of homopolymers is very poor. See Table V. The absorbency to deionized water is less than 10 grams water per gram of homopolymer, and only 10 and 20 gram synthetic urine per gram of homopolymer, respectively.

TABLE V

Control Data For Ion Pair Homopolymer

| EXP# | MOLE PERCENT MEDMA/ AMPS ® | MEDMA/MES | mole ratio* LINK | g/g** graft | DIW | SU |
|---|---|---|---|---|---|---|
| 320 | 100 | — | 0.05 | — | 8 | 10 |
| 317 | — | 100 | 0.05 | — | 9 | 20 |

MEDMA/AMPS ® = 2-methacryloyloxyethyldimethylammonium cation 2-acrylamido-2-methylpropane sulfonate anion
MEDMA/MES = 2-methacryloyloxyethyldimethylammonium cation 2-methacryloyloxyethane sulfonate anion
LINK = Methylene-bis-acrylamide Cross-Linking Agent
DIW = Deionized Water
SU = Synthetic Urine
*mole ratio = mole of the crosslinking agent per 100 mole of the ampholytic ion pair monomer and the comonomer
**g/g = absorbency units of gram aqueous liquid per gram dried polymer

EXAMPLE IV

The control data in Table VI demonstrates that although the known ampholytic ion pair 3-methacrylamidopropyltrimethylammonium 2-acrylamido-2-methylpropane sulfonate (MPTMA/AMPS ®) copolymerized with acrylamide is highly absorbent to deionized water, it is dramatically less absorbent to aqueous electrolyte solutions. The absorbency to urine is about the same as for the better of the known polymers and commercial materials. The MPTMA/AMPS ®-acrylamide copolymer also has been grafted onto starch using ceric ion or cobalt-60 irradiation. These starch grafted copolymers are poorly absorbent to deionized water, and only slightly more absorbent to synthetic urine. The better of these known polymers absorbs up to about 56 grams of urine per gram of polymer, but the starch grafted polymers absorb less than 30 grams of urine per gram of polymer.

The MPTMA/AMPS ®-acrylamide copolymers and starch grafted copolymers thereof were tested according to the method employed in Example I.

TABLE VI

Control Data For Known MPTMA/AMPS-Acrylamide Copolymers

| EXP# | MOLE PERCENT MPTMA/ AMPS ® | AM | Starch | mole ratio* LINK | g/g** DIW | SU |
|---|---|---|---|---|---|---|
| | 10 | 90 | — | — | soluble | |
| 87 | 10 | 90 | — | 0.20 | 428 | 56 |
| ** | 8.56 | 27.30 | 64.86 | — | 9.83 | 16.21 |
| ** | 8.98 | 41.76 | 49.26 | — | 11.54 | 16.62 |
| ** | 15.01 | 64.96 | 20.03 | — | 14.11 | 29.45 |

MPTMA/AMPS ® = 3-methacrylamidopropyltrimethylammonium cation/2-acrylamido-2-methylpropane sulfonate anion
AM = Acrylamide
LINK = Methylene-bis-acrylamide Cross-Linking Agent
DIW = Deionized Water
SU = Synthetic Urine
*mole ratio = mole of the crosslinking agent per 100 mole of the ampholytic ion pair monomer and the comonomer
**g/g = absorbency units of gram aqueous liquid per gram dried polymer
***J. C. Salamone, E. L. Rodriguez, K. C. Lin, L. Quach, A. C. Watterson and I. Ahmed, Polymer 26, 1234–38 (1985).

EXAMPLE V

The polysaccharide grafted MEDMA/sulfonate copolymers of the present invention in Tables VII and VIII were generally prepared according to the following two step procedure.

About 10 grams of reagent grade soluble starch was added to 70 milliliters of deionized water. While stirring under inert nitrogen atmosphere, the soluble starch slurry was heated to 95° C. for 1 hr. after which the heat was removed and the stirred soluble starch slurry was allowed to cool to room temperature, about 22° C. A solution of 0.25 gram ceric ammonium nitrate in 2 milliliters 1N nitric acid was added to the cooled stirring soluble starch slurry. After about 1 minute, the olefinic comonomer (0.1884–0.2547 moles) was then added to the soluble starch slurry mixture. The particular comonomer and relative mole percent added for each of the tested polysaccharide grafted MEDMA/sulfonate copolymers is provided in Tables VII and VIII. The mixture was stirred under inert nitrogen atmosphere for two hours.

The mixture was then heated to 60° C., at which point a solution of 0.18 g ceric ammonium nitrate in 1.5 milliliters 1N nitric acid was added to the mixture. After about 1 minute, a 32 weight percent solution of the ampholytic ion pair monomer dissolved in deionized water was added to the warmed mixture. The particulate MEDMA/sulfonate monomer and relative mole percent added for each of the tested polysaccharide grafted MEDMA/sulfonate copolymers is provided in Tables VII and VIII. This new mixture was stirred under nitrogen at 60° C. for another 4 hours.

The pH of the mixture was adjusted to between pH 4 and pH 5. The solid crude polysaccharide grafted MEDMA/sulfonate copolymer was obtained by evaporating the aqueous solvent in a forced convection oven maintained at 74° C. The crude grafted polymer was washed by boiling in dimethylformamide to remove any non-grafted acrylonitrile homopolymer. It was then thoroughly washed with deionized water to remove any water soluble polymer. The purified grafted material was finally washed with ethanol and dried in a vacuum oven at 60° C. for 24 hours. The dried polymers were then mechanically blended to a powder. The yield of polysaccharide grafted MEDMA/sulfonate copolymer was typically between 60 and 90 percent based on the total weight to the soluble starch, comonomer, and ampholytic ion pair monomer.

Some of the inventive polysaccharide grafted MEDMA/sulfonate copolymers containing an olefinic comonomer with amide, nitrile, carboxylic acid, or sulfonic acid functionalities were hydrolyzed and/or neutralized with an aqueous base such as aqueous sodium hydroxide or aqueous potassium hydroxide. The degree of hydrolysis or neutralization could be controlled by stoichiometrically limiting the amount of base relative to the amount of amide, nitrile, or carboxylic acid functionalities. For these examples, a stoichiometric excess of the amount of base was used. A suspension of 1 gram of the polymer in about 20 milliliters of 0.5 molar aqueous sodium hydroxide was heated to 95° C. until a light golden-yellow color was obtained. The mixture was then transferred to a dialysis bag with a molecular weight cut-off of 12,000–14,000 and dialyzed exhaustively against distilled water until the viscous polymer gel had reached pH 7. This viscous polymer gel was then poured into a plastic dish and dried in a forced convection oven at 74° C. The dried polymers were then mechanically blended to a powder.

The polysaccharide grafted MEDMA/sulfonate copolymers were tested according to the method employed in Example I.

TABLE VII

Comparative Data with Graft Copolymer

| Exp. | Mole Percent | | | Yield Weight Percent | XOH | DIW | SU |
|---|---|---|---|---|---|---|---|
| | MEDMA/ AMPS ® | AMPS ® | AN | | | | |
| 3B | — | — | 100 | 50 | Yes | 783 | 36 |
| 391 | — | 10 | 90 | 70 | Yes | 650 | 49 |
| 371 | 100 | — | — | 44 | | Dsp | Dsp |
| 361 | 7 | — | 93 | 83 | Yes | 565 | 73 |
| 392 | 10 | — | 90 | 60 | Yes | 603 | 70 |
| 334 | 20 | — | 80 | 84 | Yes | 349 | 64 |

MEDMA/AMPS ® = 2-methacryloyloxyethyldimethylammonium cation 2-acrylamido-2-methylpropnae sulfonate anion
AMPS ® = 2-acrylamido-2-methylpropane sulfonate (Note: AMPS is a trademark of Lubrizol for 2-acrylamido-2-methylpropane sulfonic acid.)
AN = Acrylonitril
XOH = Basic Hydrolysis and/or Neutralization with aqueous NaOH or KOH
DIW = Deionized Water
Su = Synthetic Urine
Dsp = Dispersed

TABLE VIII

Comparative Data with Graft Copolymer

| Exp | Mole Percent | | | Yield Weight Percent | XOH | DIW | SU |
|---|---|---|---|---|---|---|---|
| | MEDMA/ MES | MES | AN | | | | |
| 400 | — | 10 | 90 | — | Yes | 798 | 50 |
| 394 | 10 | — | 90 | 70 | Yes | 637 | 73 |
| 329 | 20 | — | 80 | 55 | Yes | 900 | 86 |

MEDMA/MES = 2-methacryloyloxyethyldimethylammonium cation 2-methacryloyloxyethane sulfonate anion
MES = 2-methacryloyloxyethane sulfonate anion
AN = Acrylonitrile
XOH = Basic Hydrolysis and/or Neutralization with aqueous NaOH or KOH
DIW = Deionized Water
SU = Synthetic Urine The data in Tables VII and VIII demonstrates that these polysaccharide grafted MEDMA/sulfonate copolymers exhibit significantly improved absorbency to aqueous electrolyte solutions such as urine over the absorbency of the known crosslinked polymers listed in Table III, the commercially available materials listed in Table IV, the MEDMA/sulfonate crosslinked homopolymers listed in Table V, and the MPTMA/AMPS-acrylamide copolymers listed in Table VII.

The absorbency of these polymers to urine is highly unexpected in view of the fact that the homopolymers of MEDMA/sulfonate with 0.05 weight percent crosslinking agent only absorb about 10 grams of synthetic urine per gram of the polymer. See Table V. This demonstrates that the monomers when combined into the polysaccharide grafted MEDMA/sulfonate copolymers of the present invention act synergistically to increase the absorbency of the polymers to aqueous liquids such as salt water and urine.

Taking an absorbency of about 37 grams of synthetic urine per gram of polymer as about the best of the known starch grafted polymers, the preferred polysaccharide grafted MEDMA/sulfonate copolymers of the present invention exceed this absorbency to urine by 73–132 percent (64–86 grams synthetic urine per gram of inventive polysaccharide grafted MEDMA/sulfonate copolymers, Table VII and Table VIII, compared to 37 grams urine per gram for the best of the known starch grafted polymers Table IV, Table V, and Table VI) without sacrificing absorbency to deionized water. These improved absorbencies translate into large savings in the quantity of grafted polymer required and large savings to the consumer.

Taking an absorbency of about 56 grams of synthetic urine per gram of polymer as about the best of the commercially available crosslinked polymers, the preferred polysaccharide grafted polymers of the present invention generally exceed this absorbency to urine by 14–54 percent (64.86 grams synthetic urine per gram of inventive polysaccharide grafted MEDMA/sulfonate copolymers, Table VII and Table VIII, compared to 56 grams urine per gram for the best known materials, Table III, Table IV, Table V, and Table VI) without sacrificing absorbency to deionized water. These improved absorbencies translate into large savings in the quantity of grafted polymer required.

EXAMPLE VI

A cotton graft copolymer of the present invention was prepared according to the following procedure.

About 0.23 grams of cotton gauze was soaked with a 2.66 grams aqueous solution of monomer, comonomer and crosslinking agent containing: 0.7708 grams of potassium acrylate, 0.1293 grams of acrylamide, 0.1012 grams of MEDMA/AMPS ®, 0.0006 grams of MBA and 0.0216 grams of TEMED (N,N,N',N',-tetramethylenediamine). Then 0.0038 grams of $(NH_4)_2S_2O_8$ dissolved in 1.03 grams of water was added to the solution containing the cotton gauze. The polymerization started almost instantaneously. After 2 hours, the resultant cotton graft copolymer was then washed with water several times to remove any water soluble components. The cotton graft MEDMA/AMPS ® copolymer appeared to be uniformly coated on the gauze. The graft copolymer was then air died at room temperature. The cotton graft copolymer retained the soft smooth character of the original cotton gauze. About 0.60 grams of the cotton graft copolymer was then tested for water absorbency. The cotton graft copolymer had a synthetic urine absorbency of about 33 grams of synthetic urine/gram of cotton graft copolymer. This compares very favorably to cotton gauze which absorbed only 3.7 grams of synthetic urine/gram of cotton gauze.

EXAMPLE VII

The following procedure was used to prepare a polypropylene graft copolymer containing MEDMA/AMPS.

About 0.5 grams of a nonwoven polypropylene fiber mat (denier 1–4 and Phillips Fiber source) was soaked with a solution of 0.0006 grams of MBA, 2.2161 grams of 34.78% aqueous potassium acrylate, 0.1293 grams of acrylamide, 0.2966 grams of 34.12% aqueous MEDMA/AMPS ® and 0.0216 grams of TEMED. After the mat had soaked for 30 min. a second solution containing 0.0038 grams of $(NH_4)_2S_2O_8$ in 1.03 grams of water was added to the solution containing the mat. Polymerization immediately began. After 2 hrs. the mat was removed from the solution and washed with water several times. The mat was then air dried at room temperature. The resultant mat retained its soft fiberous nature after the graft polymerization.

About 0.50 grams of grafted polypropylene mat was then tested for synthetic urine absorbency. The mat after grafting absorbed 14.4 grams of synthetic urine/gram of mat. This compares quite favorably with the water absorbency of untreated sample of the same untreated polypropylene mat which only absorbed 4.47 grams of synthetic urine/gram of polypropylene mat.

Reasonable variations can be made in view of the foregoing disclosure without departing from the spirit or scope of the present invention.

We claim:

1. A graft copolymer formed by:
   (A) graft polymerizing onto a first polymer of polypropylene; at least one comonomer selected from the group consisting of acrylamide, methacrylamide, acrylonitrile, acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and combinations of two or more thereof; and
   (B) graft copolymerizing therewith an ampholytic ion pair monomer having an ammonium cation and a sulfonate anion wherein
      (i) the ammonium cation is 2-methacryloyloxyethyldimethylammonium; and
      (ii) the sulfonate anion is selected from the group consisting of 2-acrylamido-2-methylpropane sulfonate, 2-methacryloyloxyethane sulfonate, vinyl sulfonate, styrene sulfonate and any combination of two or more thereof;
   wherein the comonomers and ion pair monomers are provided in amounts which are effective to produce a highly absorbent graft copolymer; and
   (C) partially saponifying neutralization of said graft copolymer formed in step (B).

2. The graft copolymer of claim 1 wherein
   (A) the comonomer is selected from the group consisting of acrylonitrile, acrylamide and alkali salts of acrylic acid
   (B) the ampholytic ion pair is 2-methacryloyloxyethyldimethylammonium and a sulfonate anion selected from the group consisting of 2-acrylamido-2-methylpropane sulfonate and 2-methacryloyloxyethane sulfonate.

3. The graft copolymer of claim 2 wherein the graft copolymer is composed of
   (A) from about 1 weight percent to about 50 weight percent of polypropylene; and
   (B) the mole percent of the comonomer and ampholytic ion pair grafted therewith are in the range of
      (i) from about 75 mole percent to about 98 mole percent of acrylonitrile; and
      (ii) from about 2 mole percent to about 25 mole percent of the ampholytic ion pair.

4. The graft copolymer of claim 3 wherein the graft copolymer is composed of
   (A) from 5 weight percent to about 30 weight percent of polypropylene; and
   (B) the mole percent of the comonomer and ampholytic ion pair grafted therewith are in the range of
      (i) from about 80 mole percent to about 93 mole percent of acrylonitrile; and
      (ii) from about 7 mole percent to about 20 mole percent of the ampholytic ion pair
   wherein the ampholytic ion pair is 2-methacryloyloxyethyldimethylammonium and 2-acrylamido-2-methylpropane sulfonate.

5. The graft copolymer of claim 3 wherein the graft copolymer is composed of
   (A) from about 5 weight percent to about 30 weight percent of polypropylene; and
   (B) the mole percent of the comonomer and ampholytic ion pair grafted therewith are in the range of
      (i) from about 75 mole percent to about 90 mole percent of acrylonitrile; and
      (ii) from about 10 mole percent to about 25 mole percent of the ampholytic ion pair
   wherein the ampholytic ion pair is 2-methacryloyloxyethyldimethylammonium and 2-methacryloyloxyethane sulfonate.

6. The graft copolymer of claim 2 wherein the graft copolymer is composed of
   (A) from about 1 weight percent to about 50 weight percent of polypropylene; and
   (B) the mole percent of the comonomer and ampholytic ion pair grafted therewith are in the range of
      (i) from about 80 mole percent to about 98 mole percent of acrylamide; and
      (ii) from about 2 mole percent to about 20 mole percent of the ampholytic ion pair.

7. The graft copolymer of claim 6 wherein the graft copolymer is composed of
   (A) from 5 weight percent to about 30 weight percent of polypropylene; and
   (B) the mole percent of the comonomer and ampholytic ion pair grafted therewith are in the range of
      (i) from about 85 mole percent to about 95 mole percent of acrylamide; and
      (ii) from about 5 mole percent to about 15 mole percent of the ampholytic ion pair
   wherein the ampholytic ion pair is 2-methacryloyloxyethyldimethylammonium and 2-acrylamido-2-methylpropane sulfonate.

8. The graft copolymer of claim 6 wherein the graft copolymer is composed of
   (A) from about 5 weight percent to about 30 weight percent of polypropylene; and
   (B) the mole percent of the comonomer and ampholytic ion pair grafted therewith are in the range of
      (i) from about 85 mole percent to about 90 mole percent of acrylamide; and
      (ii) from about 10 mole percent to about 15 mole percent of the ampholytic ion pair wherein the ampholytic ion pair is 2-methacryloyloxyethyldimethylammonium and 2-methacryloyloxyethane sulfonate.

9. The graft copolymer of claim 2 wherein the graft copolymer is composed of
   (A) from about 1 weight percent to about 50 weight percent of polypropylene; and
   (B) the mole percent of the comonomer and ampholytic ion pair grafted therewith are in the range of
      (i) from about 80 mole percent to about 98 mole percent of alkali salt of acrylic acid; and
      (ii) from about 2 mole percent to about 20 mole percent of the ampholytic ion pair.

10. The graft copolymer of claim 9 wherein the graft copolymer is composed of
    (A) from 5 weight percent to about 30 weight percent of polypropylene; and
    (B) the mole percent of the comonomer and ampholytic ion pair grafted therewith are in the range of
       (i) from about 85 mole percent to about 97 mole percent of alkali salts of acrylic acid; and
       (ii) from about 3 mole percent to about 15 mole percent of the ampholytic ion pair
    wherein the ampholytic ion pair is 2-methacryloyloxyethyldimethylammonium and 2-acrylamido-2-methylpropane sulfonate.

11. The graft copolymer of claim 9 wherein the graft copolymer is composed of
    (A) from about 5 weight percent to about 30 weight percent of polypropylene; and
    (B) the mole percent of the comonomer and ampholytic ion pair grafted therewith are in the range of
       (i) from about 90 mole percent to about 97 mole percent of alkali salts of acrylic acid; and
       (ii) from about 10 mole percent to about 25 mole percent of the ampholytic ion pair
    wherein the ampholytic ion pair is 2-methacryloyloxyethyldimethylammonium and 2-methacryloyloxyethane sulfonate.

12. A method of absorbing an aqueous electrolyte solution comprising contacting a graft copolymer form by:
    (A) graft polymerizing onto a first polymer of polypropylene; at least one comonomer selected from the groups consisting of acrylamide, methacrylamide, acrylonitrile acrylic acid, methacrylic acid, alkali salts of acrylic acid, alkali salts of methacrylic acid, 2-methacryloyloxyethyldimethylamine, 2-acrylamido-2-methylpropane sulfonic acid, alkali salts of 2-acrylamido-2-methylpropane sulfonic acid, 2-methacryloyloxyethane sulfonic acid, alkali salts of 2-methacryloyloxyethane sulfonic acid, N-vinyl-2-pyrrolidone and combinations of two or more thereof;
    (B) graft copolymerizing therewith an ampholytic ion pair monomer having an ammonium cation and a sulfonate anion wherein
       (i) the ammonium cation is 2-methacryloyloxyethyldimethylammonium; and
       (ii) the sulfonate anion is selected from the group consisting of 2-acrylamido-2-methylpropane sulfonate, 2-methacryloyloxyethane sulfonate, vinyl sulfonate, styrene sulfonate and any combination of two or more thereof;
    wherein the comonomers and ion pair monomers are provided in amounts which are effective to produce a highly absorbent graft copolymer; and
    (C) partially saponifying neutralization of said graft copolymer formed in step (B);
    with an electrolyte solution.

13. The method of claim 12 wherein
    (A) the comonomer is selected from the group consisting of acrylonitrile, acrylamide and alkali salts of acrylic acid
    (B) the ampholytic ion pair is 2-methacryloyloxyethyldimethylammonium and a sulfonate anion selected from the group consisting of 2-acrylamido-2-methylpropane sulfonate and 2-methacryloyloxyethane sulfonate.

14. The method of claim 13 wherein the graft copolymer is composed of
    (A) from about 1 weight percent to about 50 weight percent of polypropylene; and
    (B) the mole percent of the comonomer and ampholytic ion pair grafted therewith are in the range of
       (i) from about 75 mole percent to about 98 mole percent of acrylonitrile; and
       (ii) from about 2 mole percent to about 25 mole percent of the ampholytic ion pair.

15. The method of claim 14 wherein the graft copolymer is composed of
    (A) from 5 weight percent to about 30 weight percent of polypropylene; and
    (B) the mole percent of the comonomer and ampholytic ion pair grafted therewith are in the range of
       (i) from about 80 mole percent to about 93 mole percent of acrylonitrile; and
       (ii) from about 7 mole percent to about 20 mole percent of the ampholytic ion pair
    wherein the ampholytic ion pair is 2-methacryloyloxyethyldimethylammonium and 2-acrylamido-2-methylpropane sulfonate.

16. The method of claim 14 wherein the graft copolymer is composed of
    (A) from about 5 weight percent to about 30 weight percent of polypropylene; and
    (B) the mole percent of the comonomer and ampholytic ion pair grafted therewith are in the range of
       (i) from about 75 mole percent to about 90 mole percent of acrylonitrile; and
       (ii) from about 10 mole percent to about 25 mole percent of the ampholytic ion pair
    wherein the ampholytic ion pair is 2-methacryloyloxyethyldimethylammonium and 2-methacryloyloxyethane sulfonate.

17. The method of claim 13 wherein the graft copolymer is composed of
    (A) from about 1 weight percent to about 50 weight percent of polypropylene; and
    (B) the mole percent of the comonomer and ampholytic ion pair grafted therewith are in the range of
       (i) from about 80 mole percent to about 98 mole percent of acrylamide; and
       (ii) from about 2 mole percent to about 20 mole percent of the ampholytic ion pair.

18. The method of claim 17 wherein the graft copolymer is composed of (A) from 5 weight percent to about 30 weight percent of polypropylene; and
(B) the mole percent of the comonomer and ampholytic ion pair grafted therewith are in the range of
  (i) from about 85 mole percent to about 95 mole percent of acrylamide; and
  (ii) from about 5 mole percent to about 15 mole percent of the ampholytic ion pair
wherein the ampholytic ion pair is 2-methacryloyloxyethyldimethylammonium and 2-acrylamido-2-methylpropane sulfonate.

19. The method of claim 17 wherein the graft copolymer is composed of
(A) from about 5 weight percent to about 30 weight percent of polypropylene; and
(B) the mole percent of the comonomer and ampholytic ion pair grafted therewith are in the range of
  (i) from about 85 mole percent to about 90 mole percent of acrylamide; and
  (ii) from about 10 mole percent to about 15 mole percent of the ampholytic ion pair
wherein the ampholytic ion pair is 2-methacryloyloxyethyldimethylammonium and 2-methacryloyloxyethane sulfonate.

20. The method of claim 13 wherein the graft copolymer is composed of
(A) from about 1 weight percent to about 50 weight percent of polypropylene; and
(B) the mole percent of the comonomer and ampholytic ion pair grafted therewith are in the range of
  (i) from about 80 mole percent to about 98 mole percent of alkali salt of acrylic acid; and
  (ii) from about 2 mole percent to about 20 mole percent of the ampholytic ion pair.

21. The method of claim 20 wherein the graft copolymer is composed of
(A) from 5 weight percent to about 30 weight percent of polypropylene; and
(B) the mole percent of the comonomer and ampholytic ion pair grafted therewith are in the range of
  (i) from about 85 mole percent to about 97 mole percent of alkali salts of acrylic acid; and
  (ii) from about 3 mole percent to about 15 mole percent of the ampholytic ion pair
wherein the ampholytic ion pair is 2-methacryloyloxyethyldimethylammonium and 2-acrylamido-2-methylpropane sulfonate.

22. The method of claim 20 wherein the graft copolymer is composed of
(A) from about 5 weight percent to about 30 weight percent of polypropylene; and
(B) the mole percent of the comonomer and ampholytic ion pair grafted therewith are in the range of
  (i) from about 90 mole percent to about 97 mole percent of alkali salts of acrylic acid; and
  (ii) from about 3 mole percent to about 10 mole percent of the ampholytic ion pair
wherein the ampholytic ion pair is 2-methacryloyloxyethyldimethylammonium and 2-methacryloyloxyethane sulfonate.

* * * * *